(12) United States Patent
Deuel (10) Patent No.: US 12,035,934 B2
(45) Date of Patent: Jul. 16, 2024

(54) CONTROL MECHANISM FOR END EFFECTORS AND METHOD OF USE

(71) Applicant: Boston Scientific Scimed, Inc., Maple Grove, MN (US)

(72) Inventor: Christopher R. Deuel, Melrose, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 350 days.

(21) Appl. No.: 17/212,835

(22) Filed: Mar. 25, 2021

(65) Prior Publication Data

US 2021/0307772 A1 Oct. 7, 2021

Related U.S. Application Data

(60) Provisional application No. 63/003,329, filed on Apr. 1, 2020.

(51) Int. Cl.
| | |
|---|---|
| *A61B 17/295* | (2006.01) |
| *A61B 17/00* | (2006.01) |
| *A61B 17/068* | (2006.01) |
| *A61B 17/29* | (2006.01) |

(52) U.S. Cl.
CPC ........ *A61B 17/295* (2013.01); *A61B 17/0686* (2013.01); *A61B 2017/00367* (2013.01); *A61B 2017/2901* (2013.01); *A61B 2017/2939* (2013.01); *A61B 2017/2947* (2013.01)

(58) Field of Classification Search
CPC .............. A61B 17/295; A61B 17/0686; A61B 2017/00367; A61B 2017/2901; A61B 2017/2939; A61B 2017/2947
See application file for complete search history.

(56) References Cited

U.S. PATENT DOCUMENTS

| 5,820,009 A | 10/1998 | Melling et al. |
|---|---|---|
| 2012/0172924 A1 | 7/2012 | Allen |
| 2014/0005653 A1* | 1/2014 | Shelton, IV ........... A61B 18/14 606/205 |
| 2014/0379018 A1* | 12/2014 | Martinez ................ A61B 17/08 606/206 |

(Continued)

FOREIGN PATENT DOCUMENTS

| DE | 39 21 935 A1 | 2/1990 |
|---|---|---|
| EP | 2 653 122 A1 | 10/2013 |

(Continued)

*Primary Examiner* — Shaun L David
*Assistant Examiner* — Rachael L Geiger
(74) *Attorney, Agent, or Firm* — Bookoff McAndrews, PLLC (57) ABSTRACT

A medical device includes a shaft, an end effector at a distal end of the shaft, the end effector having a first jaw that pivots relative to a second jaw about a pivot axis, a control mechanism engaging a surface of the first jaw, such that when the control mechanism translates relative to the pivot axis from a first state to a second state, the surface of the first jaw moves relative to the control mechanism and pivot about the pivot axis. The medical device further includes an actuator extending through the shaft and coupled to the control mechanism, where translation of the actuator translates the control mechanism from the first state to the second state.

18 Claims, 8 Drawing Sheets

(56) References Cited

U.S. PATENT DOCUMENTS

| | | | |
|---|---|---|---|
| 2016/0192917 A1* | 7/2016 | Shelton, IV | A61B 17/07207 606/1 |
| 2019/0000457 A1 | 1/2019 | Shelton et al. | |
| 2019/0374297 A1* | 12/2019 | Wallace | A61B 34/71 |

FOREIGN PATENT DOCUMENTS

| WO | 2015/122998 A1 | 8/2015 |
|---|---|---|
| WO | 2018/118631 A1 | 6/2018 |
| WO | 2019/116278 A2 | 6/2019 |
| WO | 2019/217945 A1 | 11/2019 |

* cited by examiner

CONTROL MECHANISM FOR END EFFECTORS AND METHOD OF USE

CROSS-REFERENCE TO RELATED APPLICATIONS

This application claims the benefit of priority from U.S. Provisional Application No. 63/003,329, filed on Apr. 1, 2020, which is incorporated by reference herein in its entirety.

TECHNICAL FIELD

This disclosure relates to minimally invasive (e.g., endoscopic and/or laparoscopic) medical devices and related methods of use. In embodiments, the disclosure relates to one or more control mechanisms for end effectors, e.g., tissue fastening devices such as stapler devices, and related methods of use, among other aspects.

BACKGROUND

Technological developments have given users of medical systems, devices, and methods, the ability to conduct increasingly complex procedures on subjects. The coupling of tissue in, for example, a subject's gastrointestinal tract or other locations within the body, is a type of procedure in which difficulties may arise. Surgical devices that grasp or clamp tissue between opposing jaw structures and then join the tissue by surgical fasteners are known. The fasteners may include surgical staples. In some procedures, a cutting instrument may be provided to cut the tissue which has been joined by the fasteners. Drawbacks of these systems may include, for example, misalignment of jaws of the grasping or clamping devices during operation and/or increased friction forces when opening the jaws after clamping the jaws to tissue. This may result in tissue not being properly stapled and/or cut, which may increase therapy time and/or cost, and/or result in trauma to the patient. This disclosure may solve one or more of these problems or other problems in the art. The scope of the disclosure, however, is defined by the attached claims and not the ability to solve a specific problem.

SUMMARY OF THE DISCLOSURE

According to an aspect, a medical device includes a shaft, an end effector at a distal end of the shaft, the end effector including a first jaw that pivots relative to a second jaw about a pivot axis, a control mechanism engaging a surface of the first jaw, wherein the control mechanism translates relative to the pivot axis from a first state to a second state causing the surface of the first jaw to move relative to the control mechanism and pivot about the pivot axis, and an actuator extending through the shaft and coupled to the control mechanism, wherein translation of the actuator translates the control mechanism from the first state to the second state.

Translation of the control mechanism from the first state to the second state may be configured to cause the first jaw and the second jaw to transition from an open configuration to a closed configuration, respectively.

The second jaw may include a plurality of channels, and the control mechanism may be configured to move along the plurality of channels between the first state and the second state.

The second jaw may include a protrusion extending generally perpendicular to a longitudinal axis of the end effector, and wherein the protrusion may be configured to contact the control mechanism to prevent the control mechanism from translating distally of the protrusion.

The control mechanism may include a base, a distal member protruding from the base, a proximal member protruding from the base, and a slot defined between the proximal member and the distal member.

The distal member of the control mechanism may include a first surface extending from the base along a first axis, a second surface extending along a second axis, and a third surface connecting the first surface and the second surface, wherein the first axis and the second axis may not be parallel.

A camming action between the surface of the first jaw and the control mechanism may cause the first jaw to pivot about the pivot axis.

The surface of the first jaw may contact each of the first surface, the second surface, and the third surface of the distal member of the control mechanism as the control mechanism translates between the first state and the second state.

A first angle defined between the first axis and a longitudinal axis of the end effector may be up to approximately 45 degrees, and a second angle defined between the second axis and the longitudinal axis of the end effector may be less than the first angle and is up to approximately 15 degrees.

The first jaw may include a distal end and a proximal end, and the proximal end may be angled relative to the distal end.

The proximal end of the first jaw may be disposed within the slot of the control member in the first state, and wherein the proximal end may contact the distal member of the control mechanism in the second state.

The proximal end of the first jaw may contact the second surface of the control member in the second state.

The proximal end of the first jaw may include a longitudinal axis, wherein the longitudinal axis of the proximal end may be non-parallel to the first axis when the control mechanism is in the second state and, as the control mechanism moves from the second state to the first state, the longitudinal axis of the proximal end may rotate relative to the first axis such that the longitudinal axis of the proximal end and the first axis approach an approximately parallel orientation.

The proximal end of the first jaw may be configured to contact the proximal member of the control mechanism as the control mechanism moves from the second state to the first state.

The medical device may further include a pulley at a proximal end of the end effector, wherein the actuation wire may be configured to contact the pulley when the actuation wire is actuated, and wherein the pulley may be configured to contact the control mechanism and prevent the control mechanism from translating proximally of the pulley.

According to another aspect, a medical device includes an end effector including a first jaw and a second jaw coupled together and configured to move between an open configuration and a closed configuration, and a control mechanism, including, a distal member including a first surface and a second surface, a proximal member, and a slot defined between the proximal member and the distal member, wherein, in the open configuration, a surface of the first jaw is received in the slot and engages the first surface of the distal member, and in the closed configuration, the surface of the first jaw is outside the slot and engages the second surface of the distal member to inhibit relative movement of the first jaw and the second jaw.

The first jaw may include a proximal end and a distal end, wherein the proximal end may extend along a longitudinal axis, and wherein the longitudinal axis of the proximal end may be approximately parallel with a longitudinal axis of the first surface of the distal member of the control mechanism in the open configuration.

The first jaw may be configured to contact the proximal member of the control mechanism, between the closed configuration and the open configuration.

According to yet another aspect, a medical method includes advancing an end effector to a target site within a patient, wherein the end effector is inhibited from transitioning from a closed orientation to an open orientation by a control mechanism, wherein the control mechanism includes a proximal member, a distal member, and a slot defined between the proximal member and the distal member, actuating the control mechanism to transition the end effector from the closed orientation to the open orientation by overcoming a force between a proximal end of a first jaw of the end effector and the distal member of the control mechanism, wherein the proximal end of the first jaw moves into the slot as the end effector transitions from the closed orientation to the open orientation, positioning an object between the first jaw and a second jaw of the end effector, and actuating the control mechanism to create a camming action between the distal member of the control mechanism and the proximal end of the first jaw to transition the end effector from the open orientation to the closed orientation.

The control mechanism may be configured to translate relative to the end effector, and wherein the control mechanism may be positioned closer to a proximal end of the end effector when the end effector is in the open position than when the end effector is in the closed position.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

This disclosure is described with reference to exemplary medical systems and medical tools for accessing a target site, for example, for grasping, cutting, and/or stapling tissue, and providing a control mechanism for opening, closing, and/or locking jaws of these devices. This may provide improved medical tool functionality and/or may assist medical professionals to improve cutting and/or fastening of tissue. However, it should be noted that reference to any particular device and/or any particular procedure is provided only for convenience and not intended to limit the disclosure. A person of ordinary skill in the art would recognize that the concepts underlying the disclosed devices and application methods may be utilized in any suitable procedure, medical or otherwise. This disclosure may be understood with reference to the following description and the appended drawings, wherein like elements are referred to with the same reference numerals.

For ease of description, portions of the disclosed devices and/or their components are referred to as proximal and distal portions. It should be noted that the term "proximal" is intended to refer to portions closer to a user of the devices, and the term "distal" is used herein to refer to portions further away from the user. Similarly, "extends distally" indicates that a component extends in a distal direction, and "extends proximally" indicates that a component extends in a proximal direction. Further, as used herein, the terms "about," "approximately," and "substantially" indicate a range of values within +/−10% of a stated or implied value. Additionally, terms that indicate the geometric shape of a component/surface refer to exact and approximate shapes.

Embodiments of this disclosure may be used to cut and/or fasten tissue in an endo-luminal space, or facilitate the process thereof. According to an example, the fastening device may be a tissue stapling apparatus, which may include a resection or cutting mechanism (e.g., an integrated knife) and a stapling mechanism (e.g., a stapler). The fastening device may be delivered through an endoscope working channel to the target tissue site. All or parts of the fastening device could be metallic (such as stainless steel, titanium, or cobalt chrome), plastic (such as polyetheretherketone (PEEK) or the like), or include a shape memory metal (such as Nitinol), a shape memory polymer, a polymer, or any combination of materials. While reference is made herein to a fastening device with a control mechanism, the described control mechanism may be used with any set of jaws or other end effectors pivotally connected together at a distal end of a catheter, sheath, tube, or the like. The control mechanism may prevent relative (e.g., pivotal) movement between adjacent jaws and may provide improved grasping of tissues. For example, preventing pivotal rotation between adjacent jaws connected via a single, fixed pivot (e.g., as compared to jaws connected via multiple pivots, such as pivot pins, or other mechanisms) may improve alignment of the jaws, reduce friction when moving the jaws relative to each other, and reduce the size of the end effector.

Figure 1A:
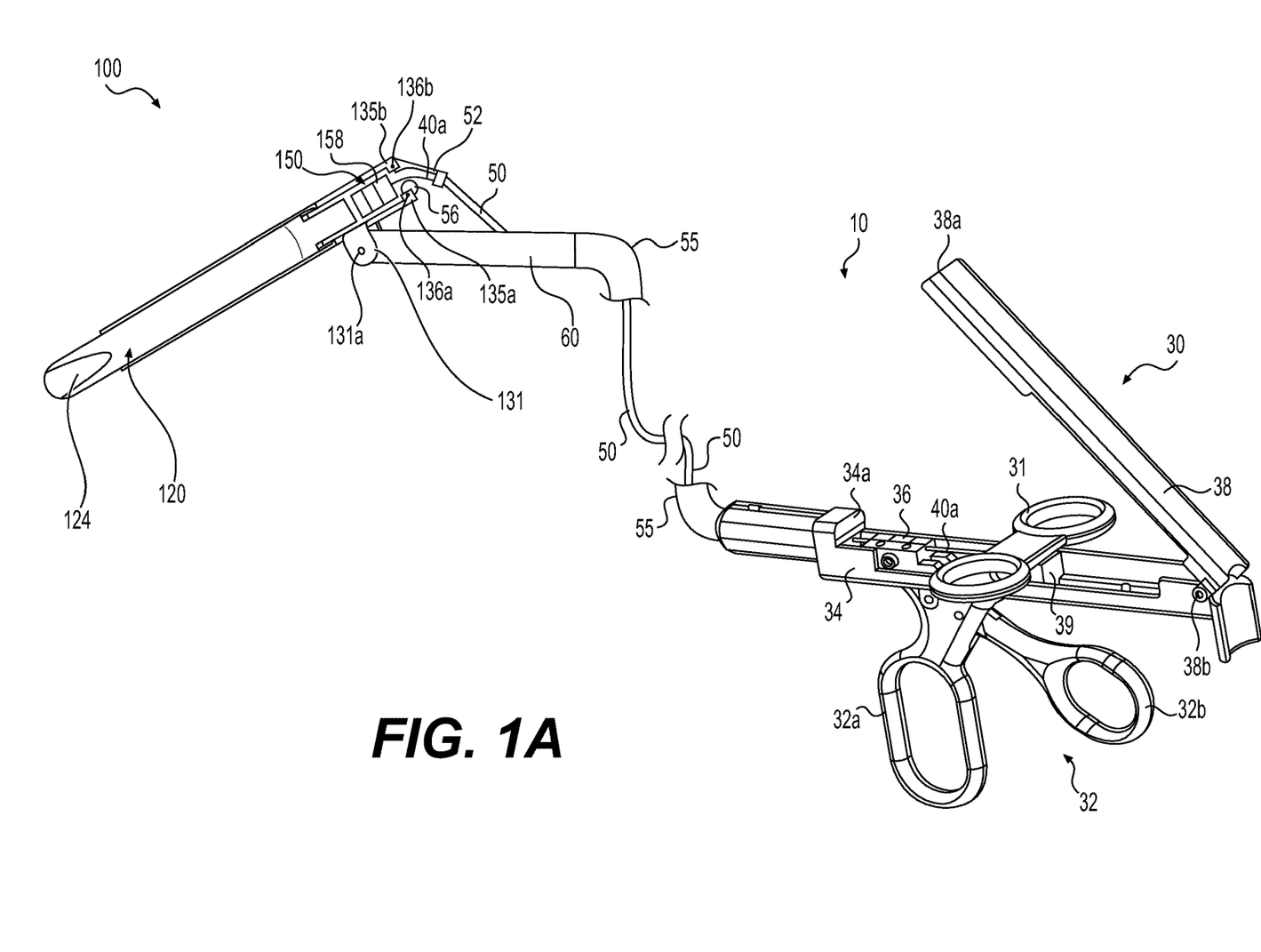
FIG. 1A is a schematic view of a medical device including an end effector, according to an embodiment.

FIG. 1A shows an apparatus 10 in accordance with an example of this disclosure. Apparatus 10 may be a surgical stapling apparatus configured to engage body tissue, and apply a plurality of fasteners thereto during minimally invasive procedures, such as laparoscopic or endoscopic procedures. In some embodiments apparatus 10 may be a suturing apparatus to deliver a suture for tissue closure during minimally invasive surgical procedures. Apparatus 10 may be used to apply a suture, clips, or other fasteners, but will be primarily discussed in the context of grasping tissue in preparation of performing additional procedures to the tissue, e.g., stapling and/or cutting the tissue.

As illustrated in FIG. 1, apparatus 10 includes a handle assembly 30 at a proximal end, an end effector 100 at a distal end, and an elongated body 50 (e.g., a shaft, a catheter, or the like) connecting a distal end of handle assembly 30 to a proximal end of end effector 100. Elongated body 50 may extend any length suitable for endoscopic or laparoscopic procedures, and may be configured to be positioned within a working channel of an endoscope. Alternatively, elongated body 50 may extend along an outer surface of the endoscope if, for example, the endoscope includes only a single lumen and/or a diameter of the lumen(s) of the endoscope are too small to receive elongated body 50. Elongated body 50 may be detachable from handle assembly 30 to facilitate insertion of elongated body 50 into a working channel of an endoscope or a channel of another device, for example by backloading elongated body 50 into the working channel. In some examples, elongated body 50 may be flexible, steerable, and/or may be rotatable about its axis. Elongated body 50 may include a lumen (or multiple lumens) for positioning actuation wires within, for actuating end effector 100 via handle assembly 30 or actuating any other portion of apparatus 10. Elongated body 50 may be configured to receive a plurality of actuation wires or a single actuation wire. In some examples, elongated body 50 may be fixedly coupled to end effector 100, and in other examples elongated body 50 may be removably or releasably coupled to end effector 100. Unless stated otherwise, any wire or actuation device described herein may extend from handle assembly 30 to end effector 100 via a lumen of elongated body 50. Alternatively, or additionally, one or more of these actuation wires or devices may extend from handle assembly 30 to end effector 100 outside of (e.g., adjacent to) elongated body 50. A catheter 55 (or any other sheath) including a lumen may extend distally from a distal end of handle assembly 30. Elongated body 50 may be disposed within the lumen of catheter 55 and may move relative to catheter 55.

Handle assembly 30 may include a handle 32 and a body 34. Handle 32 may include a fixed portion 32a and an actuator portion 32b. Fixed portion 32a of handle 32 may be fixedly coupled to body 34. Actuator portion 32b may include a circular or oval portion or ring for positioning a user's finger within, which may assist a user in holding handle assembly 30. In some examples, actuator portion 32b of handle 32 may be an actuator which may be pivotally coupled to body 34 and movable relative to fixed portion 32a of handle 32. In some examples, actuator portion 32b of handle 32 may be coupled to a proximal portion of an actuation wire, such as an actuation wire 40a, via an adjustable coupler 36, as will be described herein. A control mechanism 150 of end effector 100 may be actuated via actuation wire 40a, which extends between end effector 100 and handle assembly 30. In other examples, actuator portion 32b of handle 32 may be configured to control any other mechanism of apparatus 10, such as actuation of the deployment of staples from end effector 100 or the like. It will be understood that wire 40a may have sufficient rigidity to be pushed in the distal direction and pulled in the proximal direction.

In some examples, handle assembly 30 may include a moveable cover 38 pivotally coupled to housing 34 at pivot point 38b. In FIG. 1A, cover 38 is shown in an open position, exposing the internal portions of body 34. Cover 38 may be coupled to a proximal portion of body 34 and may cover the internal components of handle assembly 30 when positioned in a closed configuration, e.g., when a distalmost end 38a of cover 38 faces a surface 34a of body 34. Cover 38 may be positioned to cover the internal components of body 34 (e.g., a closed configuration) via a coupling mechanism at a distal portion of cover 38 and a distal portion of handle assembly 30, such as a snap-fit mechanism or the like. When in the closed configuration, cover 38 may form a pair of slots (not shown) in body 34. When the distal portion of cover 38 is uncoupled from the distal portion of body 34, a user may rotate or pivot cover 38 at pivot point 38b in order to access to the internal components of handle assembly 30.

Handle assembly 30 may include one or more adjustable couplers 36, 39, which may be configured to receive a portion of an actuation wire, such as actuation wire 40a. Any of adjustable couplers 36, 39 may be a vice which is moveable in order to clamp down onto actuation wire 40a and fixedly couple actuation wire 40a to the adjustable couplers 36, 39. In some examples, adjustable couplers 36, 39 may be moveable via a screw to adjust couplers 36, 39 and couple or uncouple actuation wire 40a from couplers 36, 39. Couplers 36, 39 may be used in the movement of additional wires described herein.

Adjustable coupler 39 may be coupled to a longitudinal actuator 31 and moveable longitudinally via translating longitudinal actuator 31 within body 34. Longitudinal actuator 31 may be partially positioned within housing 34 and may be slidable longitudinally within the two slots formed when cover 38 is positioned over the internal components of handle assembly 30. Longitudinal actuator 31 may include a pair of opposing circular or oval portions or rings, with each circular portion defining an aperture for a user to position a respective finger within. In some examples, longitudinal actuator 31 may be coupled to an actuation wire (not shown), such as via adjustable coupler 39 or via a different coupler within body 34, and may be configured to control staple deployment from end effector 100. In other examples, longitudinal actuator 31 may be configured to control any other mechanism of apparatus 10, such as proximal/distal movement of control mechanism 150 or the like. Alternatively, two actuators may be used, a first actuator for actuating a cutting device and a second actuator for actuating a stapling device.

Figure 2:
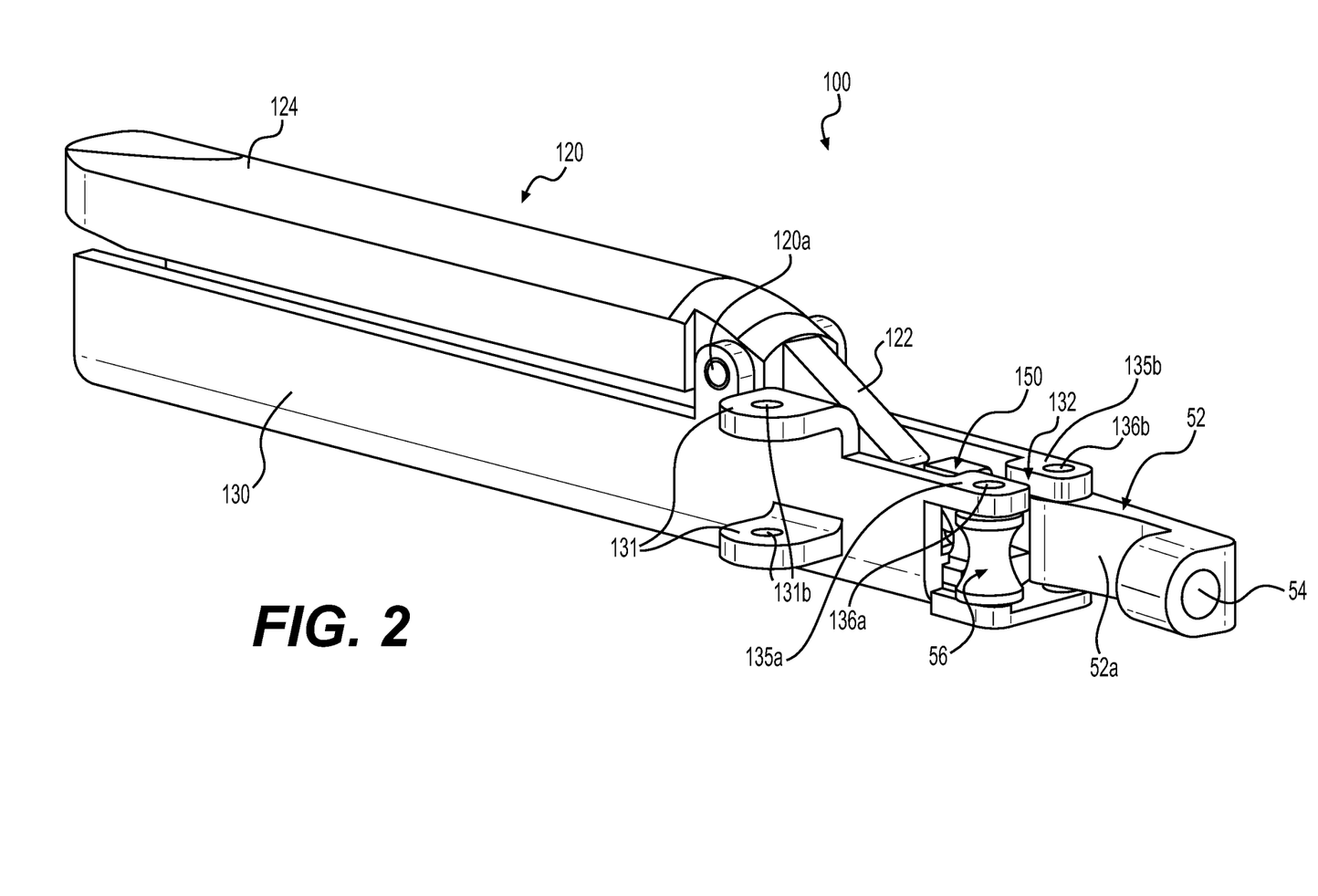
FIGS. 2-4 are views of the end effector of the medical device of FIG. 1A, according to an embodiment.

With reference to FIGS. 1A and 2, end effector 100 may include a pair of jaws, e.g., anvil 120 and a body 130 of a stapler device, which may be coupled to the distal end of elongated body 50. For example, a connector 52 at a distal end of elongated body 50 may be pivotally attached to a proximal end of end effector 100 via a first pin fixed within pinholes 136b.

Figure 1B:
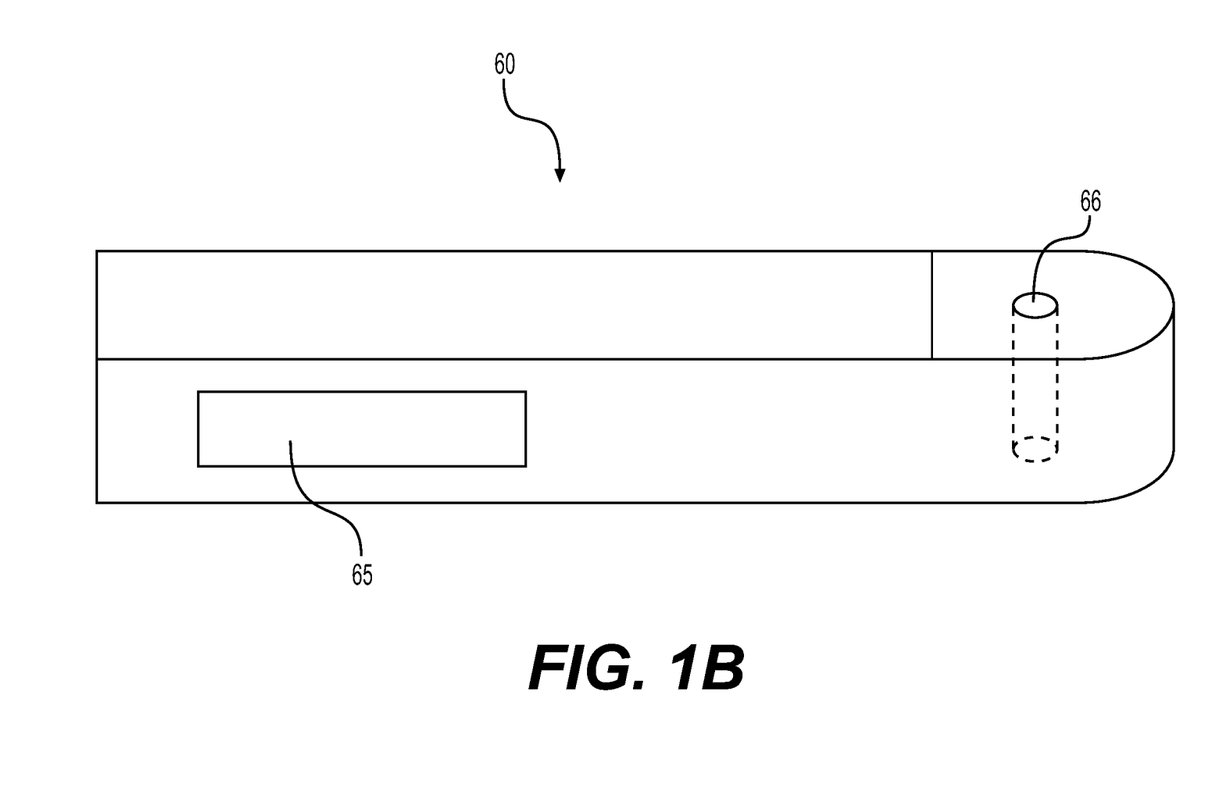
FIG. 1B is a view of a pivot arm of the medical device of FIG. 1A, according to an embodiment.

A pivot arm 60 may be pivotally attached to a side of body 130 of end effector 100 via a pin 131a (pin 131a may define a pivot axis). For example, one or more protrusions 131 may extend from the side of body 130 and may receive pin 131a through pinholes 131b in protrusions 131, thereby fixing pin 131a relative to protrusion 131. Pin 131a defines a pivot axis of end effector 100 relative to pivot arm 60. Pin 131a may also be received in an opening 66 at a distal end of pivot arm 60 (FIG. 1B), which may fix pivot arm 60 between protrusions 131, and which may allow end effector 100 to pivot relative to pivot arm 60.

Pivot arm 60 may include an opening at a proximal end. The opening may be connected to a lumen extending from the proximal end to the distal end of arm 60. A slot 65 (e.g., an opening) may be formed in a side of pivot arm 60 and may be connected to the lumen of pivot arm 60. Slot 65 may be oval, rectangular, or any other suitable shape. The proximal opening, the lumen of pivot arm 60, and slot 65 may be sized and shaped to receive a portion of elongated body 50, such that elongated body 50 may enter pivot arm 60 via the proximal opening and extend out of slot 65 (FIG. 1A). Opening 66 may be provided at a distal end of pivot arm 60. Opening 66 may receive pin 131a such that pivot arm 60 may pivot relative to pin 131a. As will be described herein, movement of elongated body 50 relative to pivot arm 60 may cause end effector 100 to rotate relative to pivot arm 60, about pin 131a. While pivot arm 60 is shown as a rectangular prism, pivot arm 60 may be any shape, including a cylinder, a rectangular prism with rounded edges, or the like. Further, pivot arm 60 may be a unitary piece with catheter 55, or pivot arm 60 may be fixedly attached to a distal end of catheter 55 by ultrasonic welding, adhesive, crimping, or the like. This may prevent pivot arm 60 from moving when elongated member 50 is moved relative to catheter 55 and/or pivot arm 60. For ease of understanding, catheter 55 is shown only in FIG. 1A.

Figure 5:
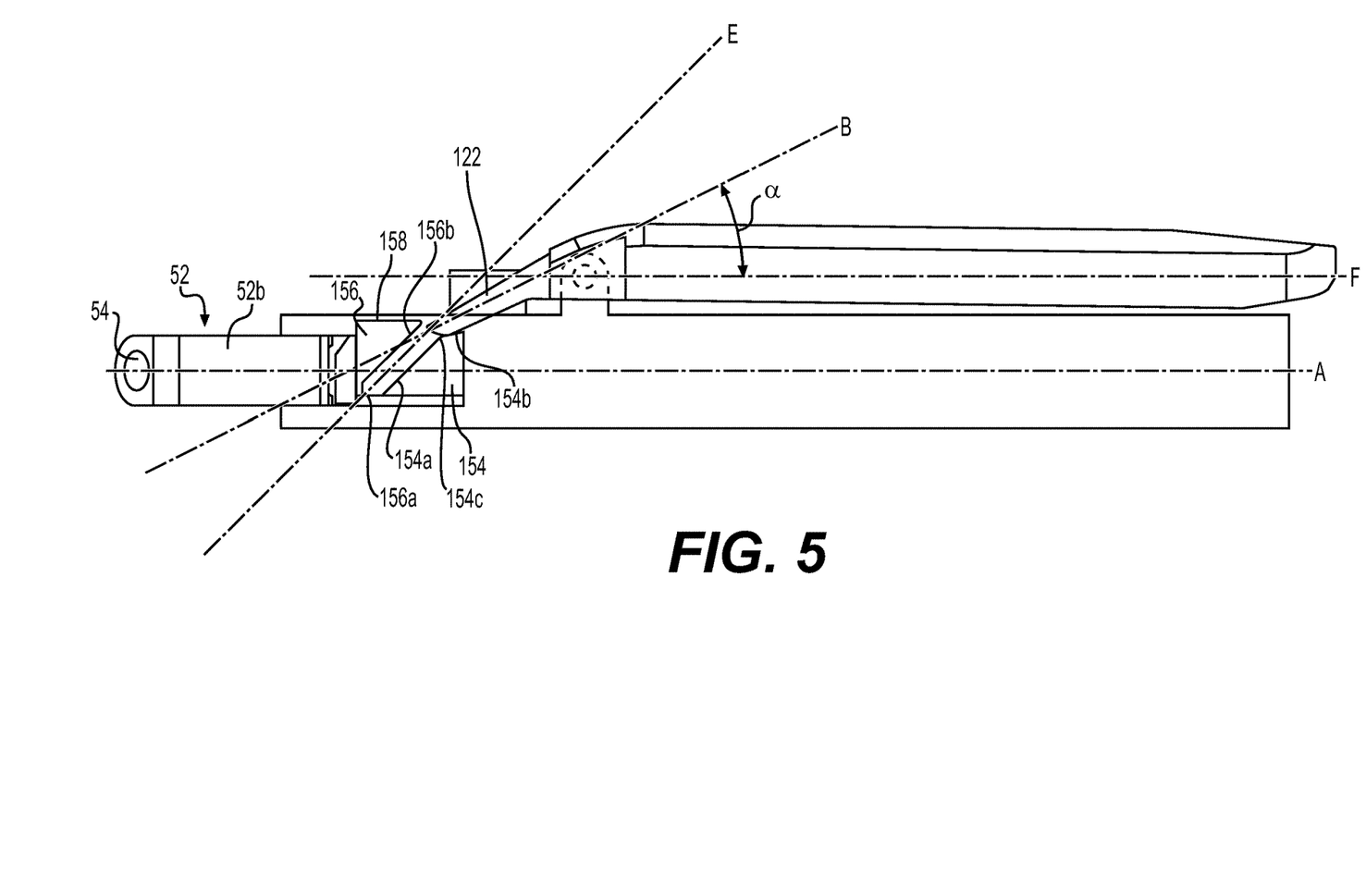
FIG. 5 is a cross-sectional view along a longitudinal axis of the end effector of FIGS. 2-4 in a closed configuration, according to an embodiment.

Anvil 120 may include a proximal end 122 and a distal end 124 and may be rotatably or pivotally coupled to body 130 via pin 120a (pin 120a may define a pivot axis). Anvil 120 and body 130 may be collectively referred to as jaws, grasping elements, and/or opposing members. In some examples, anvil 120 may be rotatably biased about pin 120a and may be biased in an open configuration or in a closed configuration. For example, distal end 124 of anvil 120 may be biased away from body 130 using a spring or the like, thereby creating a space between distal end 124 of anvil 120 and a distal portion of body 130. Alternatively, distal end 124 of anvil 120 may be biased toward body 130 using a spring or the like. As shown in FIG. 5, body 130 may include a longitudinal axis A and anvil 120 may include a longitudinal axis F (longitudinal axis A and longitudinal axis F are approximately parallel in FIG. 5). Proximal end 122 of anvil 120 may be angled relative to distal end 124 and/or longitudinal axis F, and proximal end 122 may extend along a longitudinal axis B. An angle β may be formed between longitudinal axis F and longitudinal axis B. The angle of proximal end 122 relative to longitudinal axis F may assist in opening and closing end effector 100 by allowing proximal end 122 to engage control mechanism 150 in the closed configuration and the open configuration.

Anvil 120 may rotate about pin 120a and may contact or may approach body 130 in a closed position, e.g., to retain tissue between anvil 120 and body 130. In some examples, body 130 may include a channel that supports a cartridge of staples or other fastening devices (not shown). The closed position of anvil 120 may provide a surface for which staples may be driven against when ejected from the cartridge of end effector 100. The cartridge may contain a plurality of surgical fasteners, such as staples, and the fasteners may be deployed from the cartridge when under the influence of a driving force exerted by an actuation sled or other actuation mechanism. Suitable staplers and associated actuation mechanisms are described in commonly-owned U.S. patent application Ser. No. 16/804,887, filed Feb. 28, 2020, the complete disclosure of which is incorporated herein by reference.

Figure 3:
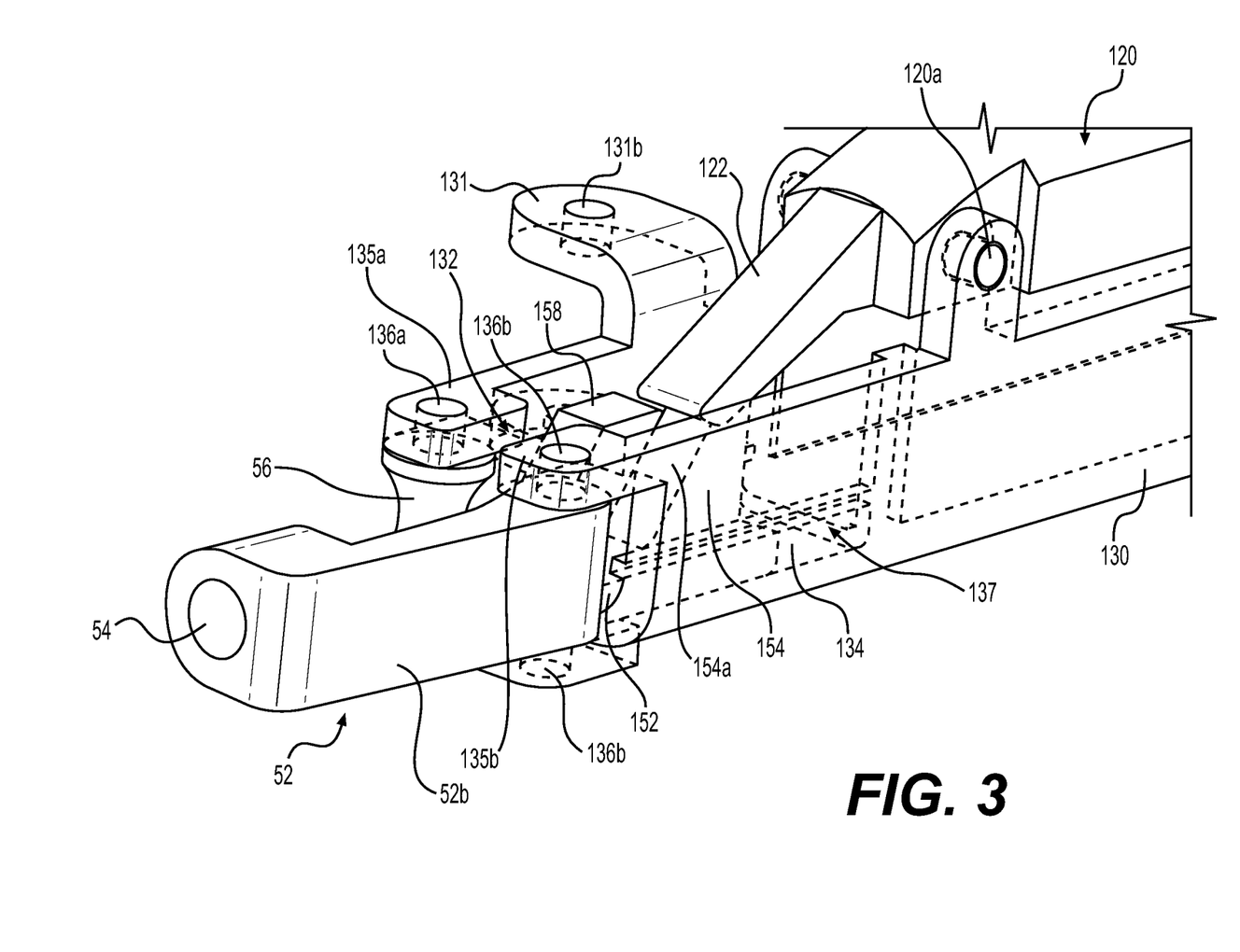
Figure 4:
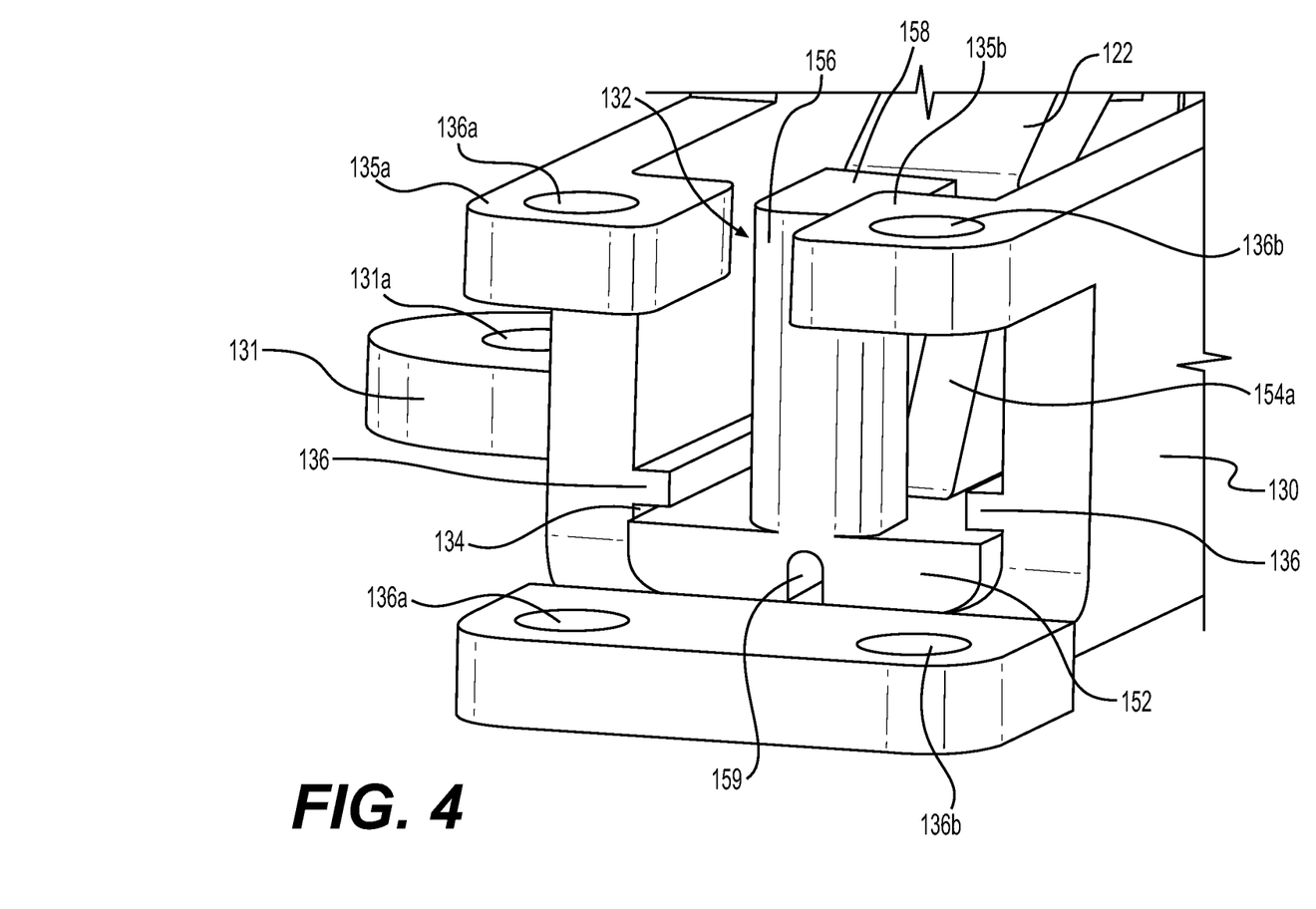

With reference to FIGS. 2-4, the proximal end of body 130 includes a first pin (the first pin may define a pivot axis) fixed in pinholes 136b to pivotally connect connector 52 to the distal end of end effector 100. A second pin (the second pin may define a pivot axis) is fixed in pinholes 136a to pivotally connect a rotatable member 56 (e.g., a pulley or a roller) to the distal end of end effector 100. The first pin may extend from pinhole 136b in the base of body 130 to pinhole 136b in a second arm 135b of body 130. A recess 132 (e.g., a slot) may be defined between first arm 135a and second arm 135b. Recess 132 may receive a portion of control mechanism 150 during operation, as will be described herein.

Rotatable member 56 may be attached on a same side of body 130 as protrusions 131, and connector 52 may be attached to an opposite side of body 130 from rotatable member 56. The second pin may extend from pinhole 136a in a base of body 130 to pinhole 136a in a first arm 135a of body 130. The rotatable member 56 may rotate about the pivot axis defined by the second pin fixed in pinholes 136a. Actuation wire 40a may contact rotatable member 56 during actuation of locking member 150 and/or based on a movement of end effector 100 relative to pivot arm 60 or a movement of end effector 100 relative to connector 52. Rotatable member 56 may rotate about the second pin fixed in pinholes 136a based on the contact between rotatable member 56, which may reduce a friction force and/or other forces on wire 40a. Connector 52 may include an inner surface 52a facing rotatable member 56 and an outer surface 52b (FIG. 3) on an opposite side from inner surface 52a. Inner surface 52a may have a curved surface, and may be concave relative to rotatable member 56 and convex relative to outer surface 52b. A hole 54 is disposed in a proximal end of connector 52. Elongated body 50 is connected to connector 52 and terminates at hole 54. Actuation wire 40a may extend from the lumen of elongated body 50 through hole 54 and may be attached at its distal end to control mechanism 150.

With reference to FIGS. 3 and 4, a pair of channels 134 (only one channel shown in FIG. 3) are defined by an inner surface of body 130. As shown in FIG. 4, channels 134 are defined between rails 136, which protrude from opposing inner sidewalls of body 130 toward a center of body 130, and a bottom inner surface of body 130. Channels 134 extend parallel to a longitudinal axis A of end effector 100 (see FIG. 5). Channels 134 define a path along which control mechanism 150 may travel, e.g., parallel to longitudinal axis A. A base 152 of control mechanism 150 may slide within channels 134 and parallel to longitudinal axis A. Rails 136 prevent movement of control mechanism 150 in a direction perpendicular to longitudinal axis A toward arms 135a, 135b. A lip 137 (e.g., a protrusion) extends from the bottom inner surface of body 130 upwards toward the center of body 130. During operation, a distal end of base 152 of control mechanism 150 may contact lip 137, which may prevent control mechanism 150 from moving distally of lip 137. A proximal end of base 152 may contact one or both of rotatable member 56 or connector 52 (FIG. 2), which may prevent control mechanism 150 from moving proximally of one or both of member 56 or connector 52.

Figure 7:
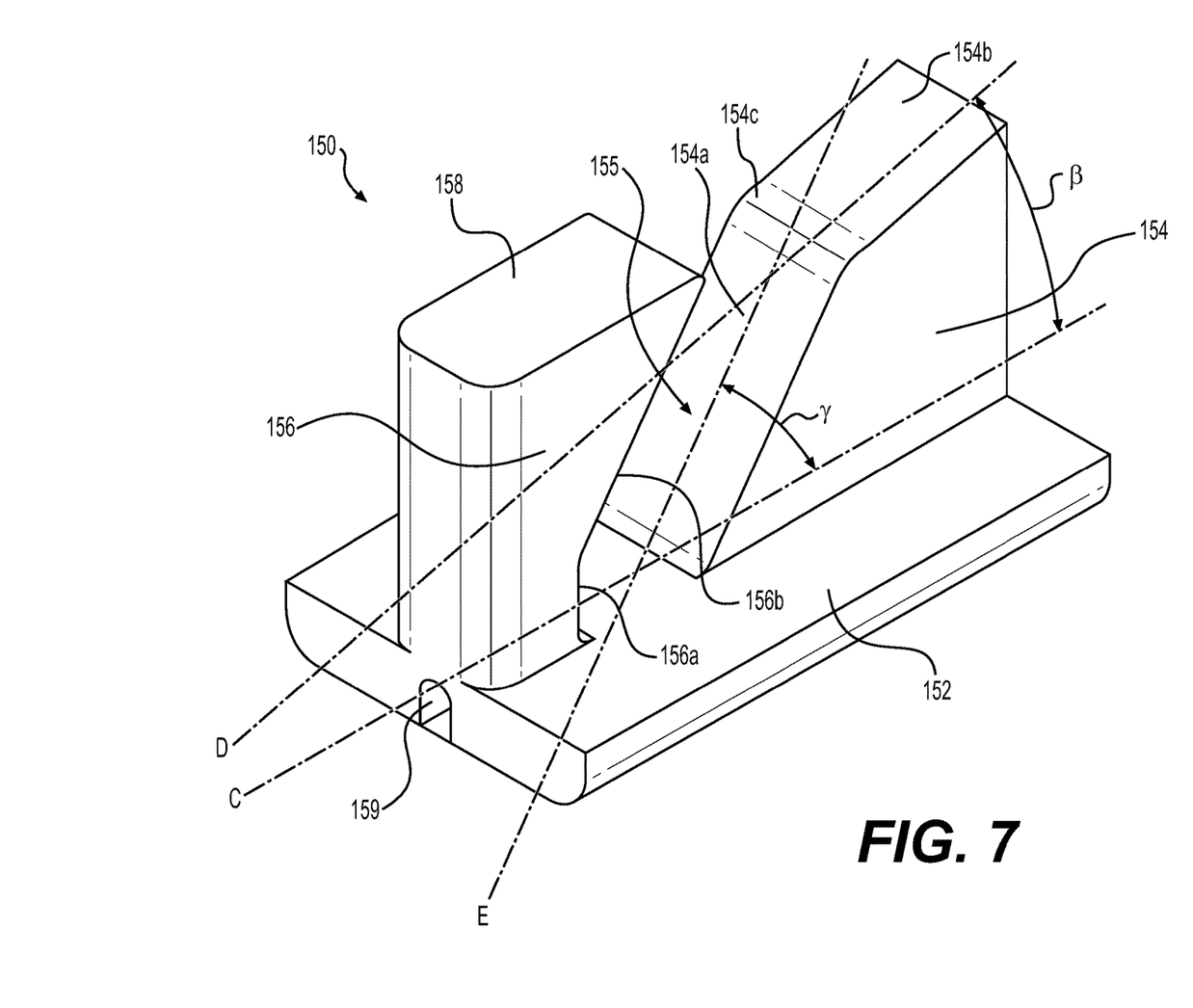
FIG. 7 is a view of a control mechanism of the medical device of FIG. 1A, according to an embodiment.

Control mechanism 150, shown in FIG. 7, includes a distal member 154 protruding from a distal end of base 152 and a proximal member 156 extending from a proximal end of base 152. Distal member 154 includes a first surface 154a, a second surface 154b, and a third surface 154c joining first surface 154a and second surface 154b. First surface 154a is generally planar and extends along a longitudinal axis E. Second surface 154b is generally planar and extends along a longitudinal axis D. First and second surfaces 154a, 154b are not limited to being planar, and may include a curved surface, e.g., a convex or a concave surface, or any other shaped surface. Third surface 154c may be generally curved, having a convex surface facing away from base 152. The shape of third surface 154c is not limited, however, and may be planar, curved in a direction different from that shown in FIG. 7, etc. As will be described herein, third surface 154c may guide proximal end 122 of anvil 120 from contacting second surface 154b to contacting first surface 154a, and from contacting first surface 154a to contacting second surface 154b during operation of control mechanism 150. This movement may be a camming action, where proximal end 122 rides along first surface 154a, second surface 154b, and third surface 154c.

Proximal member 156 may extend away from base 152. A cross-section (taken along a plane parallel to an upper surface of base 152) of proximal member 156 at or near base 152 may have a dimension smaller than a dimension of a cross-section of proximal member 156 further from base 152. For example, a third surface 156a is approximately planar and extends approximately perpendicular from base 152 and faces first surface 154a of distal member 154. Third surface 156a is joined to a fourth surface 156b at an end of third surface 156a opposite base 152. Fourth surface 156b is generally planar and angled relative third surface 156a. Fourth surface 156b faces first surface 154a and extends approximately parallel to first surface 154a and longitudinal axis E. A slot 155 is defined between first surface 154a and third and fourth surfaces 156a, 156b. Slot 155 is configured to receive proximal end 122 of anvil 120 when end effector 100 is in the open configuration. A top surface 158 defines a topmost surface of proximal member 156 and may be generally parallel to a top surface of base 152. In some instances, a distance between top surface 158 and base 152 is greater than a distance between a topmost surface of distal member 154 and base 152. During operation of control mechanism 150, proximal member 156 and/or distal member 154 may extend between first and second arms 135a, 135b and into recess 132.

A longitudinal axis C extends from the proximal end of base 152 to the distal end of base 152, and is parallel to a longitudinal axis A of end effector 100 (FIG. 5). An opening 159 extends into base 152 from the proximal end of base 152 towards the distal end of base 152 and parallel to longitudinal axis C. Opening 159 terminates proximally of the distal end of base 152. Opening 159 is configured to receive, and to fix, actuation wire 40a. Actuation wire 40a may be fixed to base 152 within opening 159, using adhesive, welding, or the like. Opening 159 may be any shape, including spherical, arch-shaped, cylindrical, or the like. In some instances, opening 159 may be open on a side of base 152 opposite proximal member 156 and distal member 154 (underneath as shown in FIG. 4), such that a portion of actuation wire 40a may be exposed from opening 159 when actuation wire 40a is attached to opening 159. Alternatively, opening 159 may be a through hole with a countersink at a distal end to receive a hypotube at a distal end of actuation wire 40a.

An angle beta may be defined between longitudinal axis D and longitudinal axis C. Angle beta may be approximately 0 degrees to 15 degrees, and may be approximately 5 degrees. An angle γ may be defined between longitudinal axis E and longitudinal axis C. Angle γ may be greater than 0 degrees and up to approximately 45 degrees, and may be approximately 30 degrees.

Figure 6:
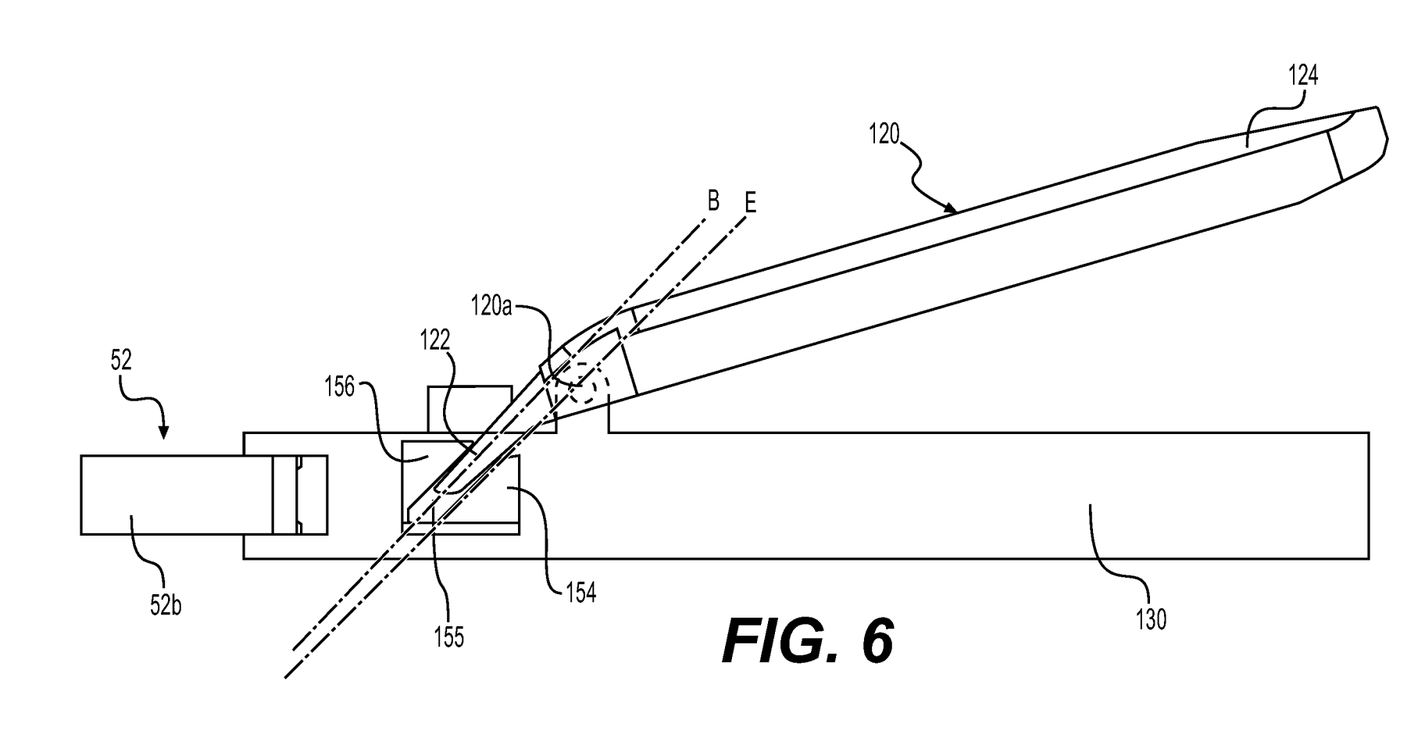
FIG. 6 is a cross-sectional view along a longitudinal axis of the end effector of FIGS. 2-4 in an open configuration, according to another embodiment.

End effector 100 is shown in a closed configuration and an open configuration in FIGS. 5 and 6, respectively. In the closed configuration, the proximal end of base 152 of control mechanism 150 is adjacent to, and/or in contact with, one or both of connector 52 or rotatable member 56. Control mechanism 150 is in its proximalmost position. In this configuration, proximal end 122 of anvil 120 contacts second surface 154b of distal member 154, thereby locking anvil 120 in the closed configuration. For example, a friction force locks proximal end 122 to second surface 154b. The friction force or other applied forces applied are sufficient to maintain anvil 120 in the closed configuration in the absence of a user interaction. The user interaction may include actuating actuation wire 40a to move control mechanism 150 in the distal direction, thereby overcoming the forces and unlocking proximal end 122 from second surface 154b. In some instances, an additional locking mechanism may be provided to assist in maintaining the open or the closed configuration of anvil 120 relative to body 130.

In the open configuration of FIG. 6, the distal end of base 152 of control mechanism 150 is adjacent lip 137 (and may contact lip 137). Control mechanism 150 is in its distalmost position, and a surface of proximal end 122 contacts third surface 156b, allowing anvil 120 to be positioned in the open configuration. A user interaction is required to move control mechanism 150 in the proximal direction, causing anvil 120 to move from the open configuration toward the closed configuration. Translation of control mechanism 150 will open and close the end effectors and lock them in the closed configuration or position them in the open configuration.

A method of operating apparatus 10 will now be described. Apparatus 10 may be introduced to a body via a natural orifice (e.g., the mouth or the anus) or via an incision or other medically-induced opening. End effector 100 may be advanced to a target site within the body via, e.g., a catheter or some other similar device. End effector 100 may be advanced along the catheter in the closed configuration, which may enable end effector 100 to navigate one or more tortuous paths within the body. Alternatively, end effector 100 may be advanced in the open configuration.

Once end effector 100 reaches the target site, end effector 100 may be maneuvered to grasp tissue or an object at the target site. End effector 100 may rotated about the pivot axes defined by the first pin fixed within pinholes 136b and/or pin 131a by, e.g., relative movement between pivot arm 60 and elongated body 50, to properly position end effector 100 relative to the target site. In this instance, end effector 100 may be in the closed position. In this position, base 152 is in its proximalmost position adjacent one or both of connector 52 or rotatable member 56. As shown in FIG. 5, second surface 154b is engaged with proximal end 122 of anvil 120, thereby locking anvil 120 in the closed configuration, as described above. Distal movement of actuation wire 40a may move control mechanism 150 in a distal direction. As control mechanism 150 moves distally, second surface 154b disengages proximal end 122. Proximal end 122 is subsequently engaged by a top portion of fourth surface 156b (in some instances, second surface 154b and fourth surface 156b may engage or contact proximal end 122 at a same time). Continued distal movement of control mechanism 150 causes proximal end 122 to move along fourth surface 156b and further into slot 155, causing anvil 120 to rotate about the pivot axis defined by pin 120a. Distal movement of control mechanism 150 is stopped by lip 137, thereby locking anvil 120 in the open configuration where longitudinal axis B is approximately parallel to longitudinal axis E.

Once in the open configuration, end effector 100 may be further maneuvered to position tissue or the object between anvil 120 and body 130. The open configuration may have an angle between anvil 120 and body 130 equal to the difference between angle γ and angle α which may be greater than 0 degrees and up to approximately 30 degrees. Subsequently, actuation wire 40a may be moved (e.g., pulled) in a proximal direction, causing control mechanism 150 to move proximally. First surface 154a may push against proximal end 122, causing anvil 120 to rotate toward the closed position. Second surface 154b may again engage proximal end 122 as control mechanism 150 approaches connector 52 and/or rotatable member 56, which further assists in rotating anvil 120 into the closed configuration. When control mechanism 150 is adjacent one or both of connector 52 or rotatable member 56, anvil 120 may be locked in the closed position, as described above, capturing tissue or the object between anvil 120 and body 130. One or more additional medical procedures, e.g., a stapling, a cutting, etc., may then be performed. After the additional medical procedure(s), the object and/or the tissue may be released by moving anvil 120 into the open configuration. Apparatus 10 may be removed from the body after all medical procedures are completed, and/or may be removed and reintroduced multiple times to perform multiple procedures within the body.

While exemplary medical systems have been described, it will be understood that the particular arrangements of elements in these fastening systems are not limited. Moreover, a size, a shape, and/or the materials of the fastening systems are not limited. As described herein, there is included a control mechanism for opening, closing, and locking an end effector. Performing various medical procedures may be improved by ensuring proper alignment of the jaws of the end effector and/or reducing the size of the end effector by reducing the number of pivot members for locking and/or opening and closing the end effector.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a shaft;
   an end effector at a distal end of the shaft, the end effector including a first jaw that pivots relative to a second jaw about a pivot axis;
   a control mechanism engaging a surface of the first jaw, wherein the control mechanism translates relative to the pivot axis from a first state to a second state causing the surface of the first jaw to move relative to the control mechanism and pivot about the pivot axis, wherein the control mechanism includes a base, a distal member protruding from the base, a proximal member protruding from the base, and a slot defined between the proximal member and the distal member, wherein a first, proximal surface of the distal member forms a closed distal end of the slot; and
   an actuator extending through the shaft and coupled to the control mechanism, wherein translation of the actuator translates the control mechanism from the first state to the second state, wherein the second jaw includes at least one channel extending parallel to a longitudinal axis of the second jaw, and wherein the control mechanism is configured to slide longitudinally along the at least one channel between the first state and the second state.

2. The medical device of claim 1, wherein translation of the control mechanism from the first state to the second state is configured to cause the first jaw and the second jaw to transition from an open configuration to a closed configuration, respectively.

3. The medical device of claim 1, wherein the second jaw includes a protrusion extending generally perpendicular to the longitudinal axis of the second jaw, and wherein the protrusion is configured to contact the control mechanism to prevent the control mechanism from translating distally of the protrusion.

4. The medical device of claim 1, wherein the first, proximal surface of the distal member of the control mechanism extends from the base along a first axis, and wherein the distal member of the control mechanism includes a second surface extending along a second axis, and a third surface connecting the first, proximal surface and the second surface, wherein the first axis and the second axis are not parallel.

5. The medical device of claim 4, wherein a camming action between the surface of the first jaw and the control mechanism causes the first jaw to pivot about the pivot axis.

6. The medical device of claim 4, wherein the surface of the first jaw contacts each of the first, proximal surface, the second surface, and the third surface of the distal member of the control mechanism as the control mechanism translates between the first state and the second state.

7. The medical device of claim 4, wherein a first angle defined between the first axis and the longitudinal axis of the second jaw is up to approximately 45 degrees, and a second angle defined between the second axis and the longitudinal axis of the second jaw is less than the first angle and is up to approximately 15 degrees.

8. The medical device of claim 4, wherein the first jaw includes a distal end and a proximal end, and the proximal end is angled relative to the distal end.

9. The medical device of claim 8, wherein the proximal end of the first jaw is disposed within the slot of the control mechanism in the first state, and wherein the proximal end contacts the distal member of the control mechanism in the second state.

10. The medical device of claim 9, wherein the proximal end of the first jaw contacts the second surface of the control mechanism in the second state.

11. The medical device of claim 8, wherein the proximal end of the first jaw includes a longitudinal axis, wherein the longitudinal axis of the proximal end is non-parallel to the first axis when the control mechanism is in the second state and, as the control mechanism moves from the second state to the first state, the longitudinal axis of the proximal end rotates relative to the first axis such that the longitudinal axis of the proximal end and the first axis approach an approximately parallel orientation.

12. The medical device of claim 8, wherein the proximal end of the first jaw is configured to contact the proximal member of the control mechanism as the control mechanism moves from the second state to the first state.

13. The medical device of claim 1, further comprising:
   a pulley at a proximal end of the end effector, wherein the actuator is configured to contact the pulley when the actuator is actuated, and wherein the pulley is configured to contact the control mechanism and prevent the control mechanism from translating proximally of the pulley.

14. A medical device, comprising:
   an end effector including a first jaw and a second jaw coupled together and configured to move between an open configuration and a closed configuration; and
   a control mechanism, including:
      a distal member including a first surface and a second surface;
      a proximal member; and
      a slot defined between the proximal member and the distal member,
   wherein, in the open configuration, a surface of the first jaw is received in the slot and engages the first surface of the distal member, and in the closed configuration, the surface of the first jaw is outside the slot and engages the second surface of the distal member to inhibit relative movement of the first jaw and the second jaw;

wherein the first jaw includes a proximal end and a distal end, wherein the proximal end extends along a longitudinal axis, and wherein the longitudinal axis of the proximal end is approximately parallel with a longitudinal axis of the first surface of the distal member of the control mechanism in the open configuration; and wherein the first jaw is configured to contact the proximal member of the control mechanism, between the closed configuration and the open configuration.

15. The medical device of claim 1:
wherein the first, proximal surface of the distal member has an angle of less than or equal to 45 degrees with respect to a longitudinal axis of the medical device.

16. The medical device of claim 15, wherein the distal member further includes a second, distal surface and a third, contact surface extending between the first, proximal surface and the second, distal surface, and wherein in the second state, a surface of the first jaw is outside the slot and engages the third, contact surface of the distal member to inhibit relative movement of the first jaw and the second jaw.

17. The medical device of claim 16, wherein the third, contact surface has an angle of less than or equal to 15 degrees with respect to the longitudinal axis.

18. The medical device of claim 14, wherein, in the open configuration, the surface of the first jaw does not contact the second surface, and wherein, in the closed configuration, the surface of the first jaw does not contact the first surface.

* * * * *